United States Patent [19]

Holtkamp

[11] Patent Number: Plant 5,601

[45] Date of Patent: Dec. 17, 1985

[54] AFRICAN VIOLET NAMED SEQUOIA

[75] Inventor: Reinhold Holtkamp, Isselburg, Fed. Rep. of Germany

[73] Assignee: Gessellschaftsvertrag uber die Ergindergemeinschaft "OPTIMARA" , Rees Haffen, Fed. Rep. of Germany

[21] Appl. No.: 568,441

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet plant named Sequoia characterized by its vigorous growth habit, dark green and shiny leaves, strong upright flower stems, each carrying 7–9 or more double frilled flowers, purple violet in flower color; profuse flowering habit, and its ability to produce a saleable attractive plant with a full flower head within 8–10 weeks after potting.

1 Drawing Figure

The present invention comprises a new and distinct cultivar of African violet plant, botanically known as *Saintpaulia ionantha,* and named Sequoia.

The new cultivar was referred to during the breeding and selection process by the designation G 9/x5, and is a product of a planned breeding program.

The new cultivar was originated from a cross made in a controlled breeding program in Isselburg, West Germany. The female, or seed parent was a cultivar designated d 150/2 red girl. The male, or pollen parent was a cultivar designated d 134/11 lilac frilled.

The new cultivar Sequoia was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Sequoia has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn. under greenhouse conditions which closely approximate those generally used in commercial practice.

The following traits have been repeatedly observed and are determined to be basic characteristics of Sequoia, which in combination distinguish this African violet as a new and distinct cultivar:

1. Vigorous growth habit.
2. Attractive dark green, shiny leaves.
3. Strong upright flower stems each carrying 7–9 or more double frilled flowers.
4. Fast growth habit, producing in 8–10 weeks after potting an attractive saleable plant with a full flower head formed of many individual double flowers.

The new cultivar is similar in many respects to the cultivar Improved Washington, disclosed in my pending patent application. Sequoia is principally distinguished from Improved Washington by its more purple and less blue flower color and by its double flower form, as opposed to the single to semi-double flower form of Improved Washington.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately noon in late November in Nashville, Tenn.

Botanical classification: *Saintpaulia ionantha,* Ramat. cv. SEQUOIA.

Parentage:

*Male parent.*—d 134/11 lilac frilled.

*Female parent.*—d 150/2 red girl.

Propagation: The new cultivar holds its distinguishing characteristics through successive propagations by leaf cuttings and by division of shoots.

Plant: From 8 cm. to 10 cm. tall when grown in pots, and approximately 25 cm. in diameter when fully grown.

*Leaves.*—General form: Oval to heart shape. Diameter: 60–65 mm. Texture: Leather-like. Aspect: Velvet to shiny and slightly hairy; serrated. Veins: Light green in color; underside veins very pronounced. Color (upperside): Yellow green 147A. Color (underside): Yellow green 147D. Petiole: Brownish green, hairy.

*Flowers.*—Buds: Ball shape. Sepals: Greenish brown, spear-shape and hairy. Calyx: Light green. Aspect: Double frilled, up to 10 petals per flower. Peduncle: Brownish, short, wire-like.

*Individual flowers.*—Size: 40–45 mm. Color: Upperside: Purple violet, somewhat darker than 82A. Underside: Purple violet 82B. Borne: On short upright peduncles, with 7–9 or more flowers being carried on each stem. Shape: Normal, two small, three large petals; most flowers are double. Corolla: Profuse and compact. Flowering time: 9 to 10 weeks after potting a saleable plant appears with full flower head.

*Reproductive organs.*—Anthers: Cells rarely visible. Styles: Rarely visible, dark purple; ovary light green.

*Roots.* —White when young and active; brownish when older.

*Disease resistance.*—Good as experienced to date.

I claim:

1. A new and distinct cultivar of African violet plant named Sequoia, as described and illustrated, and particularly characterized by its vigorous growth habit, dark green and shiny leaves, strong upright flower stems, each carrying 7–9 or more double frilled flowers, purple violet in flower color; profuse flowering habit, and its ability to produce a saleable attractive plant with a full flower head within 8–10 weeks after potting.

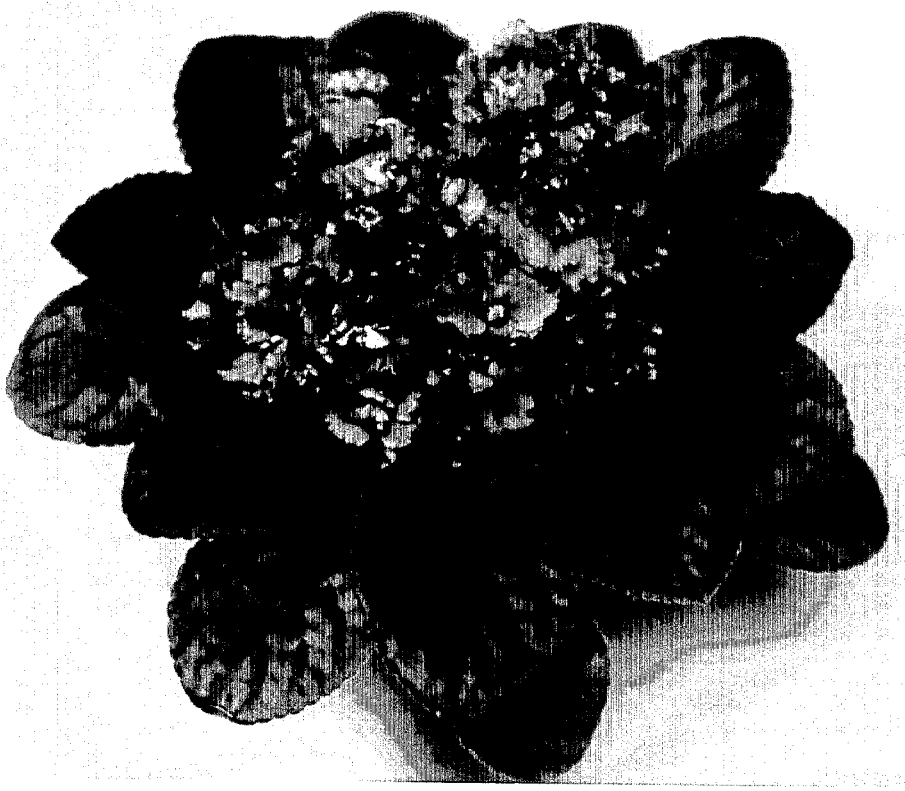

* * * * *